United States Patent [19]
Brown et al.

[11] Patent Number: 5,034,527
[45] Date of Patent: Jul. 23, 1991

[54] TRIAZINE DERIVATIVES OF MONOMERIC AND POLYMERIC HYDROXY COMPOUNDS

[75] Inventors: Sterling B. Brown, Schenectady; Ronald J. Gambale, Croton-on-Hudson; Linda L. McCracken, Clifton Park, all of N.Y.

[73] Assignee: General Electric Company, Schenectady, N.Y.

[21] Appl. No.: 495,068

[22] Filed: Mar. 19, 1990

[51] Int. Cl.$^5$ ............................................. C07D 251/30
[52] U.S. Cl. ............................................................ 544/219
[58] Field of Search ............................................ 544/219

[56] References Cited

U.S. PATENT DOCUMENTS 2,951,079  8/1960  Schroeder et al. ................. 544/219
3,156,690  11/1964  Dexter et al. ........................ 544/219
4,931,087  6/1990  Shigematsu et al. ................ 544/219

Primary Examiner—John M. Ford
Attorney, Agent, or Firm—William H. Pittman; James C. Davis, Jr.

[57] ABSTRACT

Triazine compounds are prepared by the reaction of a bisphenol, a monotetrahydropyranyl-protected bisphenol or a hydroxy-terminated polycarbonate with a chlorocyanurate containing epoxy and/or aromatic substituents. The compounds derived from bisphenols or protected bisphenols may be converted to polycarbonates, which form copolymers with other polymers containing acid or amine groups or derivatives thereof.

15 Claims, No Drawings

TRIAZINE DERIVATIVES OF MONOMERIC AND POLYMERIC HYDROXY COMPOUNDS

This invention relates to the preparation of reactively capped polycarbonates and intermediates therefor.

The superior physical properties of aromatic polycarbonates, such as high tensile and impact strength and good thermal stability, render them useful in a large number of application areas. However, polycarbonates are deficient in certain properties such as solvent resistance. Therefore, there is considerable activity in the development of blends of polycarbonates with other polymers which modify their properties. Illustrative polymers of this type are polyamides, linear polyesters and various other polymers containing amine or carboxylate groups.

The blends thus prepared are, however, often themselves deficient in properties due to the incompatibility or unfavorable morphology of the polymers comprising them. Thus, blends of polycarbonates and polyamides tend to delaminate severely. It is expected that the compatibility of such blends could be improved by incorporating therein, in various proportions, a copolymer of the blend constituents.

Polycarbonate-polyester blends are not incompatible in the same way as polycarbonate-polyamide blends; in fact, their compatibility is demonstrated by numerous commercially distributed blends of this type. Nevertheless, controlled formation of polycarbonate-polyester copolymer has the potential for improving the properties of such blends, particularly mechanical and barrier properties.

The formation of such copolymers requires the presence of functional groups on the polycarbonate which are capable of undergoing reaction with the other polymer. Thus, the functionalization of polycarbonates is a prime concern relative to the preparation of copolymers therefrom.

An illustrative method of functionalizing polycarbonates is disclosed in U.S. Pat. No. 4,732,934. In this method, a hydroxy-terminated polycarbonate is caused to react with a tricarboxylic acid derivative such as trimellitic anhydride acid chloride. Said method is, however, disadvantageous to a certain extent because it requires the use of special procedures to prepare a hydroxy-terminated polycarbonate, followed by an additional reaction (usually in solution) with the tricarboxylic acid derivative to form the functionalized polycarbonate.

Interest continues, therefore, in simplifying the procedures for preparing functionalized polycarbonates. One possible expedient is the employment of a functionalized chain termination agent in the preparation of the polycarbonate. Relatively unreactive chain termination agents such as phenol and t-butylphenol are commonly employed. Also known by way of disclosure in U.S. Pat. No. 4,853,458 and German Offenlegungsschrift 3,445,108 is the use as a chain termination agent of a carboxylated phenol or a phenol containing an olefinic functional group.

The present invention provides a class of reactively capped polycarbonates capable of undergoing addition or exchange reactions with carboxylate or amine groups in other polymers. Also included are various methods of making such reactively terminated polycarbonates, which may employ either chain termination agents or hydroxy-terminated polycarbonates.

In one of its aspects, therefore, the invention includes triazine compounds having the formula

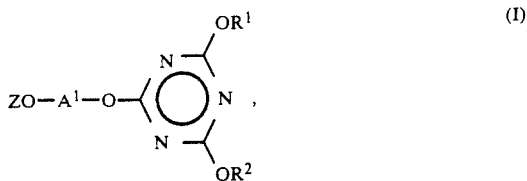

wherein:
$A^1$ is a divalent aromatic radical;
Z is hydrogen, 2-tetrahydropyranyl or a polymeric moiety comprising structural units of the formula

$A^2$ is a divalent aromatic radical;
$R^1$ is an alkyl, cycloalkyl or aromatic radical or

$R^2$ is an aromatic radical or a radical of formula III; and
$R^3$ is a divalent aliphatic, alicyclic, heterocyclic or unsubstituted or substituted aromatic hydrocarbon radical.

The triazine compounds of the present invention are of three different but related classes, which are somewhat different in their utilities. Class (1) consists of compounds in which Z is hydrogen; that is, monotriazine derivatives of dihydroxyaromatic compounds of the formula HO—$A^1$—OH. They are chiefly useful for the preparation of triazine-terminated polycarbonates, as described hereinafter.

Class (2) consists of compounds in which Z is a 2-tetrahydropyranyl radical. These compounds are in essence monotriazine derivatives of monoprotected hydroxyaromatic compounds. They may be converted to deprotected monotriazine derivatives, identical to the compounds of class (1) by acid treatment, also as described hereinafter.

In class (3), Z is a homo- or copolycarbonate moiety in which $A^2$ is a divalent aromatic radical similar, and in most cases identical, to $A^1$. Products in this class are the primary ones contemplated by the invention, and are ultimately capable of preparation from the compounds of classes (1) and (2) as well as by other methods.

Suitable $A^1$ and $A^2$ values include m-phenylene, p-phenylene, 4,4'-biphenylene, 4,4'-bi(3,5-dimethyl)phenylene, 2,2-bis(4-phenylene)propane and similar radicals such as those which correspond to the dihydroxy compounds disclosed by name or formula (generic or specific) in U.S. Pat. No. 4,217,438, the disclosure of which is incorporated by reference herein. Also included are radicals containing non-hydrocarbon moieties. These may be substituents such as chloro, nitro, alkoxy and the like, and also linking radicals such as thio, sulfoxy, sulfone, ester, amide, ether and carbonyl. Most often, however, all $A^1$ and $A^2$ radicals are hydrocarbon radicals.

The $A^1$ and $A^2$ radicals preferably have the formula $$-A^3-Y-A^4- \quad (IV)$$

wherein each of $A^3$ and $A^4$ is a monocyclic divalent aromatic radical and Y is a bridging radical in which one or two atoms separate $A^3$ from $A^4$. The free valence bonds in formula IV are usually in the meta or para positions of $A^3$ and $A^4$ in relation to Y.

In formula Iv, the $A^3$ and $A^4$ values may be unsubstituted phenylene or substituted derivatives thereof, illustrative substituents (one or more) being alkyl, alkenyl, halo (especially chloro and/or bromo), nitro, alkoxy and the like. Unsubstituted phenylene radicals are preferred. Both $A^3$ and $A^4$ are preferably p-phenylene, although both may be o- or m-phenylene or one o- or m-phenylene and the other p-phenylene.

The bridging radical, Y, is one in which one or two atoms, preferably one, separate $A^3$ from $A^4$. It is most often a hydrocarbon radical and particularly a saturated radical such as methylene, cyclohexylmethylene, 2-[2.2.1]-bicycloheptylmethylene, ethylene, isopropylidene, neopentylidene, cyclohexylidene, cyclopentadecylidene, cyclododecylidene or adamantylidene, especially a gemalkylene (alkylidene) radical. Also included, however, are unsaturated radicals and radicals which contain atoms other than carbon and hydrogen; for example, 2,2-dichloroethylidene, carbonyl, phthalidylidene, oxy, thio, sulfoxy and sulfone. For reasons of availability and particular suitability for the purposes of this invention, the preferred radical of formula IV is the 2,2-bis(4-phenylene)propane radical, which is derived from bisphenol A and in which Y is isopropylidene and $A^3$ and $A^4$ are each p-phenylene.

The $R^1$ value in formula I may be an alkyl or cycloalkyl radical, typically lower alkyl (i.e., alkyl containing up to 7 carbon atoms) and especially primary or secondary lower alkyl. It may also be an aromatic radical, typically monocyclic and containing 6-10 carbon atoms and especially an aromatic hydrocarbon radical. Finally, the $R^1$ radical may have formula III, in which $R^3$ may be aliphatic, alicyclic, aromatic (including aromatic radicals containing art-recognized substituents) or heterocyclic. It is usually lower alkylene and especially methylene.

The $R^2$ value may be an aromatic radical or may have formula III. Thus, it may have the aromatic or epoxide-containing structures previously defined for $R^1$.

Another aspect of the invention is a method for preparing the above-described triazine compounds. This method comprises effecting reaction between a hydroxy compound of the formula $ZO-A^1-OH$ and a chlorotriazine of the formula

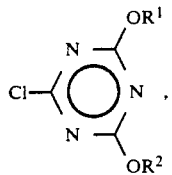

wherein $R^1$ and $R^2$ are as previously defined.

The chlorotriazines of formula V include epoxychlorotriazines, in which at least one and often both of $R^1$ and $R^2$ have formula III. Typical epoxychlorotriazines of formula V include 2-chloro-4,6-diglycidoxy-1,3,5-triazine (hereinafter "DGCC"), 2-chloro-4-methoxy-6-glycidoxy-1,3,5-triazine, 2-chloro-4-(n-butoxy)-6-glycidoxy-1,3,5-triazine (hereinafter "BGCC") and 2-chloro-4-(2,4,6-trimethylphenoxy)-6-glycidoxy-1,3,5-triazine (hereinafter "MGCC"). These compounds may also be named as though derived from cyanuric acid and designated diglycidyl chlorocyanurate, methyl glycidyl chlorocyanurate, n-butyl glycidyl chlorocyanurate and 2,4,6-trimethylphenyl glycidyl chlorocyanurate, respectively. They may be prepared, for example, by the reaction of 2,4,6-trichlorotriazine (cyanuric chloride) with glycidol or combinations thereof with n-butanol, methanol or mesitol, as disclosed in U.S. Pat. No. 4,895,945. Cyanuric chloride and n-butyl dichlorocyanurate are both commercially available.

The compounds of formula V also include arylchlorotriazines, in which at least one and often both of $R^1$ and $R^2$ are aromatic radicals. Substituted phenyl groups in which the substituents have several identical hydrogen atoms, such as t-butylphenyl and methoxyphenyl, have the advantage of affording products in which the proportion of capping may be determined by proton nuclear magnetic resonance, utilizing the protons on the t-butyl or methoxy group. On the other hand, electron-withdrawing substituents such as halo, carboxy, carbalkoxy, nitrile, nitro, acyl and aldehyde groups may promote displacement by amine groups in a polyamide by reason of the lower pKa of the conjugate acid of the displaced aryloxide anion.

Typical arylchlorotriazines include 2-chloro-4,6-diphenoxy-1,3,5-triazine, 2-chloro-4,6-di-(4-t-butylphenoxy)-1,3,5-triazine and 2-chloro-4,6-di-(4-methoxyphenoxy)-1,3,5-triazine. When named as though derived from cyanuric acid, these compounds are designated diphenyl chlorocyanurate, di-(4-t-butylphenyl) chlorocyanurate and di-(4-methoxyphenyl) chlorocyanurate, respectively. They may be similarly prepared by the reaction of 2,4,6-trichlorotriazine (cyanuric chloride) with the corresponding hydroxyaromatic compounds, or sequentially with hydroxyaromatic compounds and aliphatic or alicyclic alcohols.

The reaction between the chlorotriazine and the dihydroxy compound may be conducted at temperatures in the range of about 35°-75° C. An organic solvent, typically a chlorinated aliphatic hydrocarbon such as methylene chloride or chloroform, is typically employed, and a basic reagent such as an alkali metal hydroxide or an amine is preferably employed as a catalyst and/or hydrogen chloride scavenger. Preferably, an alkali metal hydroxide is added incrementally. There may also be employed a phase transfer catalyst; any of such catalysts which are stable and effective under the prevailing reaction conditions may be used. Those skilled in the art will be able to choose suitable phase transfer catalysts. Particularly preferred are the tetraalkylammonium chlorides wherein at least two alkyl groups per molecule, typically 2 or 3, contain about 5-20 carbon atoms.

In order to have utility for the purposes of the invention, it is necessary for triazine compounds of class (1) as defined hereinabove (i.e., those prepared from dihydroxyaromatic compounds of the formula $HO-A^1-OH$) to have one free hydroxy group. Such triazine compounds are therefore preferably prepared by using a large excess of dihydroxyaromatic compound, typically about a 300-800% molar excess. On the other hand, for compounds of classes (2) and (3) (i.e., those prepared from tetrahydropyranyl-protected dihydroxyaromatic compounds or in which Z is a polycarbonate moiety) the proportions of reagents employed may be stoichiometric or near-stoichiometric; however, it is frequently advantageous to employ up to about a 10% excess of one of the reagents, typically the hydroxyaromatic compound.

Following completion of the reaction, it is frequently preferred to neutralize the mixture and convert salts of the hydroxyaromatic compounds to the free hydroxy species. This is often conveniently done by adding gaseous or solid carbon dioxide.

Compounds of class (1) are generally obtained in admixture with a large proportion of excess dihydroxyaromatic compound, by reason of the proportions of reagents used in their preparation. For use as chain termination agents in polycarbonate preparation as described hereinafter, they need not be isolated but may be used in crude form. If isolation of such compounds, either from excess dihydroxyaromatic compound or from other materials present in a deprotection reaction, is desired, it may be accomplished by flash chromatography with mixtures of non-polar and relatively polar solvents, the polar solvent being employed in progressively greater proportions as the chromatography proceeds.

The principal utility of the compounds of class (2) (i.e., those in which Z is 2-tetrahydropyranyl) is as intermediates in a second method of preparation of the compounds of class (1), by way of deprotection. Such deprotection may be accomplished by reaction with an acid in an effective amount to cleave the tetrahydropyranyl groups from the polymer chain, ordinarily in a relatively polar aqueous or non-aqueous medium. The acid should be soluble in said medium; suitable acids include those which achieve deprotection but which will not cleave the triazine compound in other locations, such as in epoxy groups. Acetic acid is frequently preferred.

Compounds of class (3), in which Z is a polymeric moiety, may be prepared in a number of ways. In the first place, they are capable of direct preparation by reaction of a chlorotriazine of formula V with a hydroxy-terminated polycarbonate. Hydroxy-terminated polycarbonates may in turn be prepared by known transesterification reactions, by chain cleavage of a higher molecular weight polycarbonate, or by phosgenation with the employment of a tetrahydropyranyl ether as a chain termination agent as disclosed in the aforementioned U.S. Pat. No. 4,736,013, followed by deprotection by a procedure similar to that discussed hereinabove.

In the second place, compounds of class (3) may be prepared by employing a compound of class (1) as a chain termination agent in a conventional polycarbonate formation reaction. Such reactions typically involve interfacial phosgenation or bischloroformate reaction, in a mixture of water and a substantially water-immiscible organic liquid such as methylene chloride, under alkaline conditions and most often in the presence of an amine such as triethylamine as catalyst. The compound of class (1) is incorporated in proportions to afford a polycarbonate product of the desired molecular weight. This reaction is so well known to those in the art that an extended discussion thereof is unnecessary.

The preparation of the triazine compounds of this invention is illustrated by the following examples. All percentages are by weight. Molecular weights herein were determined by gel permeation chromatography relative to polystyrene.

EXAMPLE 1

A solution of 43.70 grams (192 mmol.) of bisphenol A, 12.30 grams (38 mmol.) of MGCC and 750 ml. of methylene chloride was stirred as 3.40 grams (42.5 mmol.) of 50% aqueous sodium hydroxide solution was added over ½ hour. After sodium hydroxide addition was complete, the mixture was heated under reflux for 18 hours. It was then cooled to room temperature and neutralized to a pH of 7 by the addition of solid carbon dioxide. The neutralized mixture was filtered and the filtrate was dried over anhydrous magnesium sulfate, filtered and vacuum stripped to yield the impure mono(epoxytriazine) derivative of bisphenol A as a thick oil. The crude material was useful as a chain termination agent for polycarbonates; however, separation of the pure triazine compound was achieved by flash chromatography with mixtures of ethyl ether and pentane.

EXAMPLE 2

A mixture of 3.218 grams (10 mmol.) of MGCC, 3.511 grams (10.5 mmol.) of the mono-(2-tetrahydropyranyl) ether of bisphenol A and 20 ml. of methylene chloride was stirred as a solution of 440 mg. (11 mmol.) of sodium hydroxide in 1 ml. of water was added. Stirring at room temperature was continued for 24 hours, after which the mixture was diluted with 50 ml. of methylene chloride, washed with two 75-ml. portions of water and one 75-ml. portion of 2% aqueous hydrochloric acid solution, dried over sodium sulfate, filtered and vacuum stripped. The crude product was the desired triazine derivative.

EXAMPLE 3

The crude product of Example 2 was dissolved in a mixture of 32 ml. of glacial acetic acid, 16 ml. of tetrahydrofuran and 8 ml. of water and stirred at room temperature for 24 hours. The mixture was diluted with 200 ml. of ethyl ether and 250 ml. of water and solid sodium bicarbonate was added to bring it to a pH of 7. The organic layer was separated, washed with 250 ml. of water and 200 ml. of saturated aqueous sodium chloride solution, dried over magnesium sulfate, filtered and vacuum stripped. Upon flash chromatography as described in Example 1, the pure mono(epoxytriazine) derivative of bisphenol A was isolated as a white foamy solid.

EXAMPLE 4

A mixture of 20.6 grams (50 mmol.) of 2-chloro-4,6-di-(t-butyl)phenoxytriazine, 57 grams (250 mmol.) of bisphenol A, 1 liter of methylene chloride and 13 grams of a 10% solution in toluene of a commercially available tetraalkylammonium chloride as a phase transfer catalyst was stirred at room temperature as 20 grams (50 mmol.) of 10% aqueous sodium hydroxide solution was added over 30 minutes. Stirring was continued for 3 hours, after which the organic layer was separated, washed twice with aqueous sodium chloride solution and dried over magnesium sulfate. Upon vacuum stripping of solvent, the desired crude monotriazine derivative of bisphenol A was obtained as a mixture comprising about 20% of said derivative, with the balance being bisphenol A.

EXAMPLE 5

A mixture of 19.09 grams (84 mmol.) of bisphenol A, 1.511 grams (2.94 mmol.) of the chromatographically purified product of Example 1, 85 mg. (7.6 mmol.) of triethylamine in the form of a 5% solution in methylene chloride, 57 ml. of methylene chloride and 50 ml. of deionized water was charged to a five-necked Morton flask fitted with a pH probe, reflux condenser, phosgene dip tube, mechanical stirrer and addition funnel. Phosgene was bubbled into the mixture at 610 mg. per minute for 17 minutes, to a total of 10.37 grams (104.7 mmol.), with addition of 50% aqueous sodium hydroxide solution to maintain the pH at about 11. A total of 17.5 ml. of sodium hydroxide solution was added. The mixture was diluted with 150 ml. of methylene chloride, washed once with 0.5% aqueous hydrochloric acid solution and three times with water, and precipitated by pouring into one liter of methanol in a blender. Upon filtration and vacuum drying at 80° C., the desired epoxytriazine-capped polycarbonate was obtained; it had a weight average molecular weight of 61,100 and a number average molecular weight of 20,400, and was shown by high field proton nuclear magnetic resonance spectroscopy to contain a substantial proportion of aryloxyglycidoxytriazine end groups.

EXAMPLE 6

The procedure of Example 5 was repeated, employing 21.485 grams (110 mmol.) of bisphenol A, 111 mg. (10 mmol.) of triethylamine, 75 ml. of methylene chloride, 65 ml. of water and 13.6 grams (137.4 mmol.) of phosgene added at 800 mg. per minute over 17 minutes, and substituting 5.839 grams of the product of Example 4 (3.85 mmol. of monotriazine derivative) for the product of Example 1. The resulting aryloxytriazine-capped polycarbonate had a weight average molecular weight of 45,500 and a number average molecular weight of 9,700. It was shown by high field proton nuclear magnetic resonance spectroscopy to contain a substantial proportion of diaryloxytriazine end groups.

EXAMPLE 7

A bisphenol A polycarbonate having a weight average molecular weight of about 188,000 was degraded by extrusion on a twin-screw extruder at 288° C., yielding a hydroxy-terminated polycarbonate having a molecular weight of about 74,500. A solution of 3 grams of the hydroxy-terminated polycarbonate, 100 mg. of DGCC and about 0.2 ml. of pyridine in 25 ml. of chloroform was heated under reflux for 30 minutes. The product was precipitated by pouring the solution into methanol in a blender and was filtered, washed with methanol and dried in a vacuum oven. It was shown by proton nuclear magnetic resonance spectroscopy to contain about 0.48% epoxytriazine moieties.

EXAMPLE 8

A hydroxy-terminated bisphenol A polycarbonate having an intrinsic viscosity (in chloroform at 25° C.) of 0.38 dl./g. was prepared by the reaction of bisphenol A with diphenyl carbonate. A mixture of 400 grams of the hydroxy-terminated polycarbonate, 12 grams of DGCC, 48 grams of a 10% solution in toluene of a methyltrialkylammonium chloride in which the alkyl groups contained 8-10 carbon atoms (a phase transfer catalyst) and 2500 ml. of methylene chloride was stirred vigorously at room temperature and 24 grams of a 10% aqueous sodium hydroxide solution was added dropwise, with stirring which was continued for 30 minutes after base addition was complete. The product was precipitated by pouring the solution into methanol in a blender and dried in a vacuum oven. It had an intrinsic viscosity of 0.21 and was shown by proton nuclear magnetic resonance spectroscopy to contain about 0.67% epoxytriazine moieties.

The triazine compounds of this invention in class (3) (i.e., the triazine-capped polycarbonates) form compatible copolymer-containing compositions with other polymers containing acid or amine groups or functional derivatives thereof. Such other polymers include polyamides and polyesters as well as olefin polymers containing such groups. Compositions of this type are disclosed and claimed, in copending, commonly owned application Ser. No. 07/495,071.

Polyesters suitable for preparing such compositions generally comprise structural units of the formula

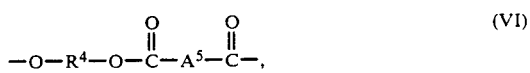

wherein each $R^4$ is independently a divalent aliphatic, alicyclic or aromatic hydrocarbon or polyoxyalkylene radical and $A^5$ is a divalent aromatic radical. They include thermoplastic polyesters illustrated by poly(alkylene dicarboxylates), elastomeric polyesters, polyarylates, and polyester copolymers such as copolyestercarbonates. Because the principal reaction which occurs with the epoxy groups in the capped polycarbonate involves a carboxylic acid group of the polyester, it is highly preferred that said polyester have a relatively high carboxylic end group concentration. Concentrations in the range of about 5-250 microequivalents per gram are generally suitable, with 10-100 microequivalents per gram being preferable, 30-100 being more preferable and 40-80 being particularly desirable.

The polyester may include structural units of the formula

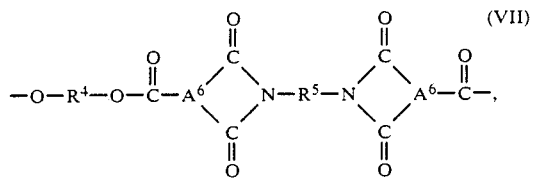

wherein $R^4$ is as previously defined, $R^5$ is a polyoxyalkylene radical and $A^6$ is a trivalent aromatic radical. The $A^5$ radical in formula VI is most often p- or m-phenylene or a mixture thereof, and $A^6$ in formula VII is usually derived from trimellitic acid and has the structure

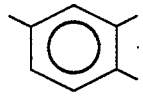

The $R^4$ radical may be, for example, a $C_{2-10}$ alkylene radical, a $C_{6-10}$ alicyclic radical, a $C_{6-20}$ aromatic radical or a polyoxyalkylene radical in which the alkylene groups contain about 2-6 and most often 4 carbon atoms. As previously noted, this class of polyesters includes the poly(alkylene terephthalates) and the polyarylates. Poly(alkylene terephthalates) are frequently preferred, with poly(ethylene terephthalate) and poly(butylene terephthalate) being most preferred.

The polyester generally has a number average molecular weight in the range of about 20,000–70,000, as determined by intrinsic viscosity (IV) at 30° C. in a mixture of 60% (by weight) phenol and 40% 1,1,2,2-tetrachloroethane.

Any polyamide made by any known method may be used in the preparation of copolymer-containing compositions. Polyamides in which the amine end group concentration is at least about 60 meq./g. are particularly useful, but the invention also contemplates the use of polyamides with lower amine end group concentration or, in the case of epoxytriazine-terminated polycarbonates, with carboxylic acid end groups.

Suitable polyamides include those of the type prepared by the polymerization of a monoamino-monocarboxylic acid or a lactam thereof having at least 2 carbon atoms between the amino and carboxylic acid group, of substantially equimolar proportions of a diamine which contains at least 2 carbon atoms between the amino groups and a dicarboxylic acid, or of a monoaminocarboxylic acid or a lactam thereof as defined above together with substantially equimolar proportions of a diamine and a dicarboxylic acid. The dicarboxylic acid may be used in the form of a functional derivative thereof, for example, an ester or acid chloride.

Examples of the aforementioned monoaminomonocarboxylic acids or lactams thereof which are useful in preparing the polyamides include those compounds containing from 2 to 16 carbon atoms between the amino and carboxylic acid groups, said carbon atoms forming a ring with the —CO—NH— group in the case of a lactam. As particular examples of aminocarboxylic acids and lactams there may be mentioned ε-aminocaproic acid, butyrolactam, pivalolactam, ε-caprolactam, capryllactam, enantholactam, undecanolactam, dodecanolactam and 3- and 4-aminobenzoic acids.

Diamines suitable for use in the preparation of the polyamides include the straight chain and branched chain alkyl, aryl and alkaryl diamines. Illustrative diamines are trimethylenediamine, tetramethylenediamine, pentamethylenediamine, octamethylenediamine, hexamethylenediamine (which is often preferred), trimethylhexamethylenediamine, m-phenylenediamine and m-xylylenediamine.

Suitable dicarboxylic acids include those which contain an aliphatic or aromatic group containing at least 2 carbon atoms separating the carboxy groups. The aliphatic acids are often preferred; they include sebacic acid, octadecanedioic acid, suberic acid, glutaric acid, pimelic acid and adipic acid.

Both crystalline and amorphous polyamides may be employed, with the crystalline species often being preferred by reason of their solvent resistance. Typical examples of the polyamides or nylons, as these are often called, include, for example, polyamide-6 (polycaprolactam), 66 (polyhexamethylene adipamide), 11, 12, 63, 64, 6/10 and 6/12 as well as polyamides from terephthalic acid and/or isophthalic acid and trimethylhexamethylenediamine; from adipic acid and m-xylylenediamines; from adipic acid, azelaic acid and 2,2-bis(p-aminophenyl)propane or 2,2-bis-(p-aminocyclohexyl)propane and from terephthalic acid and 4,4'-diaminodicyclohexylmethane. Mixtures and/or copolymers of two or more of the foregoing polyamides or prepolymers thereof, respectively, are also within the scope of the present invention. Preferred polyamides are polyamide-6, 66, 11 and 12, most preferably polyamide-66.

The olefin polymers (hereinafter sometimes designated "polyolefins") which may be used in the preparation of copolymer-containing compositions are homopolymers and copolymers of known aliphatic olefins including ethylene, propylene, 1-butene, 2-butene, 1-pentene, 2-pentene, 2-methyl-1-pentene, 3-methyl-1-pentene, 1-octene and 1-dodecene. The $C_{2-6}$ olefins are preferred, with ethylene and propylene being most preferred.

For the purposes of the invention, it is essential for the polyolefin to have groups capable of reactions involving the epoxy groups or phenoxy groups in the polycarbonate. Those skilled in the art will be familiar with suitable substituents; examples are carboxylic acid groups and anhydrides and acidic esters thereof, sulfonic acid groups and amine groups. The carboxylic acid-derived groups are preferred by reason of their availability and the high stability of copolymers prepared therefrom.

The substituents may be incorporated in the polyolefin by employing suitable functional comonomers, such as acrylic acid, maleic anhydride or allylamine, in the formation thereof. They may also be provided by graft polymerization on an already prepared polyolefin, using the same monomers, or by other art-recognized means of functionalization.

Either solution or melt blending procedures may be employed for the preparation of the copolymer-containing compositions. Typical reaction temperatures are in the range of about 175°–350° C. Thus, relatively high boiling solvents such as o-dichlorobenzene, 1,2,4-trichlorobenzene or 1,2,3,4-tetrachlorobenzene are preferred for solution reactions.

Melt reaction procedures are frequently preferred because of the availability of melt blending equipment in commercial polymer processing facilities. Conventional equipment of this type is suitable, with the use of extrusion equipment generally being convenient and therefore often preferred.

The copolymer-containing compositions may also contain conventional ingredients such as fillers, flame retardants, pigments, dyes, stabilizers, anti-static agents, crystallization aids, mold release agents and the like. Resinous components not previously discussed, especially elastomeric impact modifiers, may also be present.

The preparation of copolymer-containing compositions from the triazine-capped polycarbonates of this invention is illustrated by the following examples.

EXAMPLES 9–15

Mixtures of 5 grams of the epoxytriazine-capped polycarbonate of Example 5, 5 grams of various carboxy-functionalized or anhydride-functionalized olefin polymers and 100 ml. of 1,2,3,4-tetrachlorobenzene were heated at 265° C. for 1 hour, with stirring. The mixtures were then cooled, precipitated by pouring into 1 liter of methanol in a blender and filtered. The filtration residues were reslurried three times with additional 1-liter portions of methanol, filtered after each operation and vacuum dried for 4 hours at 80° C.

About 10 grams of each dried product was accurately weighed and extracted in a Soxhlet extractor with 300 ml. of chloroform over 18 hours. The extraction residue and the residue obtained by evaporating the chloroform were dried and weighed and the percentage of copolymer formation determined therefrom. The results are given in the following table.

| Example | Olefin polymer | Copolymer, % |
|---------|---------------|--------------|
| 9 | Ethylene-acrylic acid (8%) | 30 |
| 10 | Propylene-acrylic acid (6%) | 30 |
| 11 | Propylene-maleic anhydride (0.5%), hydrolyzed | 40 |
| 12 | Ethylene-maleic anhydride, hydrolyzed | 10 |
| 13 | Ethylene-maleic anhydride (1.25%) | 10 |
| 14 | Propylene-maleic anhydride (0.5%) | 15 |
| 15 | Propylene-styrene-maleic anhydride | 25 |

EXAMPLE 16

A dry blend of 250 grams of the epoxytriazine-capped polycarbonate of Example 5 and 250 grams of a commercially available styrene-maleic anhydride copolymer containing 14% maleic anhydride was tumble mixed and extruded on a twin-screw extruder at temperatures in the range of 125°–265° C. The extrudate was quenched in water, pelletized and dried in an air-circulating oven for 4 hours at 100° C. After drying, it was extracted with ethyl acetate in a Soxhlet extractor. The weights of extracted material and residue showed the presence of 17% copolymer.

EXAMPLE 17

A mixture of equal weights of the aryloxytriazine-capped polycarbonate of Example 6 and a commercially available polyamide-6 was heated at 260° C. for about 8 minutes, with stirring. Upon cooling, Soxhlet extraction with chloroform and analysis, it was found that about 11% copolymer was present.

What is claimed is:

1. A triazine compound having the formula

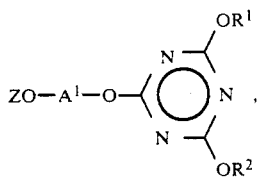 (I)

wherein:
Z is hydrogen, 2-tetrahydropyranyl or a polycarbonate moiety comprising structural units of the formula

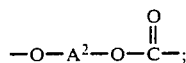 (II)

each of $A^1$ and $A^2$ is m-phenylene, p-phenylene, 4,4'-biphenylene, 4,4'-bi(3,5-dimethyl)phenylene or 2,2-bis(4-phenylene)propane;

$R^1$ is a monocyclic $C_{1-7}$ alkyl, cycloalkyl or $C_{6-10}$ unsubstituted or substituted aromatic hydrocarbon radical or

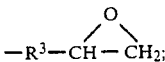 (III)

$R^2$ is a monocyclic $C_{6-10}$ aromatic hydrocarbon radical or a radical of formula III; and
$R^3$ is a lower alkylene radical.

2. A compound according to claim 1 wherein $A^1$ has the formula

 (IV)

wherein each of $A^3$ and $A^4$ is unsubstituted or alkyl-, alkenyl-, halo- nitro- or alkoxy-substituted phenyl and Y is methylene, cyclohexylmethylene, 2-bicycloheptyl-methylene, ethylene, isopropylidene, neopentylidene, cyclohexylidene, cyclopentadecylidene, cyclododecylidene or adamantylidene.

3. A compound according to claim 2 wherein Z is hydrogen.

4. A compound according to claim 3 wherein each of $A^3$ and $A^4$ is p-phenylene and Y is isopropylidene.

5. A compound according to claim 3 wherein at least one of $R^1$ and $R^2$ has formula III.

6. A compound according to claim 5 wherein $R^3$ is methylene.

7. A compound according to claim 6 wherein one of $R^1$ and $R^2$ is a $C_{6-10}$ aromatic hydrocarbon radical.

8. A compound according to claim 3 wherein each of $R^1$ and $R^2$ is a $C_{6-10}$ aromatic hydrocarbon radical.

9. A compound according to claim 2 wherein Z is 2-tetrahydropyranyl.

10. A compound according to claim 9 wherein each of $A^3$ and $A^4$ is p-phenylene and Y is isopropylidene.

11. A compound according to claim 9 wherein each of $R^1$ and $R^2$ is glycidyl or a $C_{6-10}$ aromatic hydrocarbon radical.

12. A compound according to claim 2 wherein Z is a polycarbonate moiety and each of $A^1$ and $A^2$ has the formula

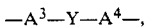 (IV)

wherein each of $A^3$ and $A^4$ is unsubstituted or alkyl-, alkenyl-, halo- nitro- or alkoxy-substituted phenyl and Y is methylene, cyclohexylmethylene, 2-bicycloheptyl-methylene, ethylene, isopropylidene, neopentylidene, cyclohexylidene, cyclopentadecylidene, cyclododecylidene or adamantylidene.

13. A compound according to claim 12 wherein $A^2$ and $A^3$ are each p-phenylene and Y is isopropylidene.

14. A compound according to claim 12 wherein at least one of $R^1$ and $R^2$ is glycidyl.

15. A compound according to claim 12 wherein at least one of $R^1$ and $R^2$ is a $C_{6-10}$ aromatic hydrocarbon radical.

* * * * *